United States Patent
Böse

[19]

[11] Patent Number: 6,124,103
[45] Date of Patent: Sep. 26, 2000

[54] ARRANGEMENT AND METHOD OF EXAMINING HYDROPHILIC MACROMOLECULES IN AN AQUEOUS SOLUTION

[75] Inventor: Matthias Böse, Karlsruhe, Germany

[73] Assignee: Bruker Analytik GmbH, Rheinstetten, Germany

[21] Appl. No.: 09/250,258

[22] Filed: Feb. 16, 1999

[30] Foreign Application Priority Data

Feb. 27, 1998 [DE] Germany .......................... 198 08 226

[51] Int. Cl.⁷ .......................... G01N 33/53; G01N 21/29; G01N 33/558; G01N 33/543; G61K 39/395; G61K 9/14; G01D 11/26; G01F 1/01

[52] U.S. Cl. .................. 435/7.1; 435/7.5; 435/6; 422/50; 422/82.05; 422/82.06; 422/119; 422/82.11; 424/178.1; 424/179.1; 424/484; 424/489; 424/502; 436/518; 436/524; 436/527; 436/528; 436/531; 436/532; 436/533; 436/63; 436/71; 436/86; 436/823; 436/829; 436/56; 250/304; 250/330; 250/338.1; 250/338.2; 250/339.14; 250/354.1

[58] Field of Search ...................... 436/518, 524, 436/527, 528, 531–533, 63, 71, 86, 823, 829, 56; 435/7.1, 7.5, 6; 424/178.1, 179.1, 484, 489, 502; 250/304, 330, 338.1, 338.2, 339.14, 354.1; 422/50, 82.05, 82.06, 119, 82.11

[56] References Cited

U.S. PATENT DOCUMENTS

| | | | |
|---|---|---|---|
| Re. 34,312 | 7/1993 | Geiger et al. | 435/5 |
| 4,175,864 | 11/1979 | Gilby | 356/326 |
| 4,348,329 | 9/1982 | Chapman | 260/403 |
| 4,670,386 | 6/1987 | Sugaar | 435/29 |
| 4,752,572 | 6/1988 | Sundberg et al. | 435/7 |
| 4,874,710 | 10/1989 | Piran | 436/518 |
| 4,880,731 | 11/1989 | Kaspar | 435/7 |
| 4,933,114 | 6/1990 | O'Brien et al. | 260/403 |
| 4,935,339 | 6/1990 | Zahradnik | 435/5 |

(List continued on next page.)

FOREIGN PATENT DOCUMENTS

43 23 487   1/1995   Germany .

OTHER PUBLICATIONS

Biophys. J. 1991, Columw 59, pp. 387–396: Darst et al.: "Two–dimensional crystal of streptavidin on . . . ".

Current Opinion in Structural Biology, 1991, 1(4) pp. 642–646: Kronberg et al.: "Two–dimensional crystals of proteins on lipid layers".

*Primary Examiner*—Christopher L. Chin
*Assistant Examiner*—Pensee T. Do
*Attorney, Agent, or Firm*—Paul Vincent

[57] ABSTRACT

An arrangement for the investigation of hydrophilic macromolecules (1) in an aqueous solution having a solid carrier surface (5) onto which a lipid film (24) is disposed, wherein the molecules (1) to be investigated are bound, by means of a molecular coupling system (20), to the lipid film (24) and thus are immobilized, is characterized in that the molecular coupling system (20) comprises at least two, preferably three molecular or nuclear components (21, 22, 23), which can be coupled to each other, of which a first component (21) is bound to the lipid film (24) and a second component (22) is bound to a hydrophilic macromolecule (1) to be investigated. In this way, it is rendered possible to immobilize and investigate any hydrophilic macromolecules, wherein the coating of the solid carrier surface should be able to be carried out in an as easy as possible and reversible manner.

16 Claims, 1 Drawing Sheet

U.S. PATENT DOCUMENTS

| | | | |
|---|---|---|---|
| 4,959,303 | 9/1990 | Milburn et al. | 435/7 |
| 4,966,839 | 10/1990 | Kaspar | 435/7 |
| 4,975,581 | 12/1990 | Robinson et al. | 250/339 |
| 5,000,960 | 3/1991 | Wallach | 424/450 |
| 5,093,580 | 3/1992 | Sting | 250/571 |
| 5,097,129 | 3/1992 | De Vries et al. | 250/338 |
| 5,126,241 | 6/1992 | Schenk | 435/7.1 |
| 5,229,611 | 7/1993 | Ukon | 250/347 |
| 5,234,812 | 8/1993 | Buck et al. | 435/7.5 |
| 5,527,711 | 6/1996 | Tom-Moy et al. | 436/518 |
| 5,553,616 | 9/1996 | Ham et al. | 128/633 |
| 5,567,591 | 10/1996 | Lovell et al. | 435/7 |
| 5,622,872 | 4/1997 | Ribi | 436/518 |
| 5,643,731 | 7/1997 | Bosslet et al. | 435/7.1 |
| 5,694,930 | 12/1997 | Pries et al. | 128/633 |
| 5,729,018 | 3/1998 | Wells et al. | 250/339 |
| 5,746,217 | 5/1998 | Erickson et al. | 128/760 |
| 5,754,715 | 5/1998 | Melling | 385/12 |
| 5,754,722 | 5/1998 | Melling | 385/115 |
| 5,866,430 | 9/1999 | Grow | 436/172 |
| 5,945,674 | 8/1999 | Dukor | 250/339 |

ARRANGEMENT AND METHOD OF EXAMINING HYDROPHILIC MACROMOLECULES IN AN AQUEOUS SOLUTION

BACKGROUND OF THE INVENTION

The invention concerns an arrangement and a method of examining hydrophilic macromolecules in an aqueous solution having a solid carrier surface provided with a lipid film, wherein the molecules to be examined are bound to the lipid film by means of a molecular coupling system and thus are rendered immobile.

Such an arrangement and a corresponding operational method are known from Liu et al., Eur. Biophys. (J. 1995) 24: 31–38.

Hydrophilic proteins have been investigated for some time by means of FT-IR-ATR technology. In this connection, they are usually disposed in dissolved form onto an ATR crystal and are immobilized by drying. Then, FT-IR spectra are recorded from the dried protein films. The dried proteins are dissolved by adding water. In order to be able to study the interaction between hydrophilic proteins and other molecules, the proteins have to be present in the aqueous environment in their native form. As a consequence, for such investigations by means of ATR technology, the proteins should be present in a form bound to the ATR crystal in a "water-proof" manner.

From Blankenburg et al., Biochemistry (1989) 28: 8214–8221 an arrangement is known for the examination of streptavidin by means of UV light in an area of 230 nm, wherein the extremely high affinity of the protein streptavidin for the cyclic urea derivative biotin (vitamin H; bonding constant: $10^{15}$ $M^{-1}$), which has been known for more than 20 years and has been utilized in connection with the most different applications in biotechnology, is utilized for attaching streptavidin to be examined to biotinylated phospholipids. In this known method, the lipids are arranged again in a monolayer on a water surface.

Darst et al., Biophys. J. (1991) 59: 387–396 disclose on the one hand an arrangement for the examination of lipid films by means of electron diffraction, wherein crystalline streptavidin is arranged on a teflon trough and, on its side facing away from the teflon trough, is bound to biotinylated lipids. Furthermore, this publications also discloses an arrangement in which the hydrophilic protein Ferritin is bound to crystallized streptavidin by biotin residues. In this connection, the use of lipids in the arrangement to be examined is again not mentioned.

The publication "PE Applied Biosystems report" of the company Perkin Elmer, 1/1997, page 21, describes an arrangement for the examination of interactions between membranes and proteins in an aqueous medium, in which by means of weakened total reflection infrared spectroscopy (ATR-IR) the electrostatic connection of the protein Trypsin Inhibitor to a membrane in buffered water with defined pH value was measured. To this end, a lipid double layer of a thickness of approximately 5 nm (so-called solid-supported membrane=simple model of a biological membrane) was applied to the surface of a Germanium-ATR-crystal, and on the surface thereof facing away from the ATR crystal, the protein to be examined, from an aqueous solution, was added.

The initially cited article by Liu et al., Eur. Biophys. J. (1995) 24, 31–38 finally describes a system, wherein a lipid monolayer is arranged on a hydrophobic silicon surface, which is biotinylated on its side facing away from the silicon, wherein the biotin molecules again are bound to avidin molecules. The latter are examined optically by means of dispersion of He—Ne laser light in an area of 633 nm. This system is suited only for measurements with one particular protein, namely avidin, which can be immobilized on the biotin lipid film due to its high bonding affinity for biotin.

In contrast thereto, it is the object of the present invention to present an arrangement and a method of the initially mentioned type, which enable immobilization and examination of any hydrophilic macromolecules, wherein it should be possible to coat the solid carrier surface in an as easy as possible and reversible manner.

SUMMARY OF THE INVENTION

According to the invention, this object is achieved in that the molecular coupling system comprises at least two molecular or nuclear components, which can be coupled to one another, of which a first component is bound to the lipid film and a second component is bound to the hydrophilic macromolecules to be examined.

Compared to the above described known prior art systems, the system according to the invention is considerably more variable due to the numerous possibilities of selecting the components of the molecular coupling system in view of the possibilities of examining hydrophilic macromolecules, and provides an almost unlimited number of different possibilities of application in a surprisingly simple but effective manner.

One embodiment of the inventive arrangement is particularly preferred wherein the molecular coupling system comprises a third component which connects the first and the second component.

In this manner, the variability of the investigation system with respect to the known one-component coupling systems is considerably increased.

Preferably, the first and second components are chemically identical, which considerably simplifies the selection of the third component since the latter merely needs to have two chemically identical docking points.

A further development is particularly preferred in which the first and the second components are biotin, the third component is avidin and/or streptavidin.

The bond between biotin and avidin or streptavidin has already been largely examined, as mentioned above, and is well known and the extremely high bonding constant of approximately $10^{15}$/Mol turns this arrangement into an almost ideal coupling system.

In an alternative, the first and the second components may be an antigen, the third component may be an associated antibody. A system of this type is particularly cheap and easy to produce and comprises also a high bonding constant.

One embodiment of the inventive arrangement is also particularly preferred, in which the lipid film is formed as a double layer, which is known per se i.a. from the above-cited publication by the company Perkin Elmer. The production of such a double lipid film is considerably more simple and thus cheaper than disposing a lipid monolayer. If possible, the lipid double layer can be easily removed from the solid carrier surface (moist cotton cloth) after the measurement and the carrier surface is available for further coatings. The lipid film can also be in the form of packed vesicles.

In preferred embodiments of the invention, the hydrophilic macromolecules to be examined comprise proteins, peptides, DNA, RNA or whole procariotic or eucariotic cells. Examination of other groups of hydrophilic macromolecules by means of the arrangement according to the invention is also feasible.

In a further embodiment of the inventive arrangement, the solid carrier surface is part of an amorphous solid which may comprise in particular silver halides, chalcogenides, glass or quartz.

Of particular importance is an alternative embodiment of the inventive arrangement, wherein the solid carrier surface forms part of the crystalline solid.

In particularly preferred further developments of the two above-mentioned embodiments, the solid carrier surface comprises an ATR (attenuated total reflection) element, in particular ATR fibers or ATR crystals, e.g. zinc selenide, thallium bromide, germanium or diamond.

An ATR arrangement of this type is e.g. also described in DE-196 12 877 C1.

Included in the scope of the present invention is also a method of investigating hydrophilic macromolecules in aqueous solution, which is carried out with an inventive arrangement of the above-mentioned type. Through immobilization of the molecules to be examined, on the solid carrier surface, a relatively high concentration of the molecules to be examined is achieved resulting in a high yield of information signals and thus high sensitivity and good resolution of the corresponding investigation method.

The hydrophilic macromolecules are preferably examined by electromagnetic radiation.

In an advantageous further development of this variant of the method, an optical method is used for the examination of the hydrophilic macromolecules. The macromolecules to be examined are, in general, particularly easy to characterize owing to their optical properties.

In this connection, it is again preferred to use IR (infrared) radiation for the examination of the hydrophilic macromolecules, since in this manner the molecular vibrations can be detected which are highly specific and thus render the method particularly sensitive. For the examination of the hydrophilic macromolecules it is preferred to use an ATR (attenuated total reflection) method whose mode of operation and advantages are described e.g. in the above cited publication DE 196 12 877 C1. Due to the high concentration of the macromolecules to be examined owing to their immobilization on the solid carrier surface by means of the inventive arrangement, a particularly large signal yield and particularly high sensitivity can be achieved.

One variant of the method is of particular advantage, in which a flow cell is used for guiding the aqueous solution past the solid carrier surface of an ATR element provided with the immobilized hydrophilic macromolecules.

A flow cell of this type is also described in DE 196 12 877 C1 but also in the above-cited publication of the company Perkin Elmer. The advantages of the flow cell are also known from literature.

For the examination of the hydrophilic macromolecules it is particularly preferred to utilize radiation in the mid infrared range (MIR). In comparison with visible light or near infrared (=NIR) light, the MIR light penetrates deeper into the examination arrangement and the absorption degree obtained is higher than e.g. in the NIR range, such that the sensitivity of the method is higher.

In an alternative, it is possible to use Raman dispersion for the investigation of the hydrophilic macromolecules. This method provides essentially molecular information which is complementary to the information obtained according to the above-described MIR method.

Further advantages of the invention can be gathered from the description and the drawing. The features mentioned above and below may also be used according to the invention either individually or collectively in arbitrary combinations. The embodiments shown and described are not to be regarded as exhaustive enumeration but rather have exemplary character for describing the invention.

The invention is shown in the drawing and is explained in more detail by means of embodiments. In the drawing:

DESCRIPTION OF THE PREFERRED EMBODIMENTS

For an examination of hydrophilic macromolecules, in particular proteins, the investigation objects should be immobilized in a suitable manner to be concentrated, in order to be able to carry out measurements on the macromolecules. The macromolecules to be examined may be any proteins, peptides, DNA, RNA or whole procariotic or eucariotic cells. For the examination it is proposed to bind the hydrophilic macromolecules via a molecular coupling system which comprises at least two molecular or nuclear components, which can be coupled to each other, to a lipid film which again is disposed on a solid carrier surface.

Figure 1:
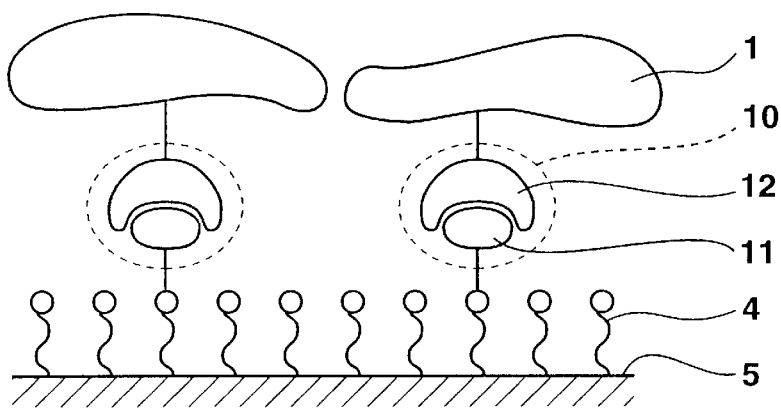
FIG. 1 shows a schematic representation of a simple embodiment of the inventive arrangement with a two-component molecular coupling system and a lipid monolayer.

FIG. 1 shows a simple embodiment of such an inventive arrangement: A lipid film 4 is disposed on a solid carrier surface 5 in the form of a monolayer. A first component 11 of a two-component molecular coupling system 10 is attached covalently to the lipid film 4, while a second component 12 of the coupling system 10 is attached to the macromolecules 1 to be examined.

Through coupling of the two components 11, 12, the macromolecules 1 are immobilized on the carrier surface 5.

By means of said two-component coupling system 10 completely different macromolecules 1 may be coupled to the lipid film 4.

Figure 2:
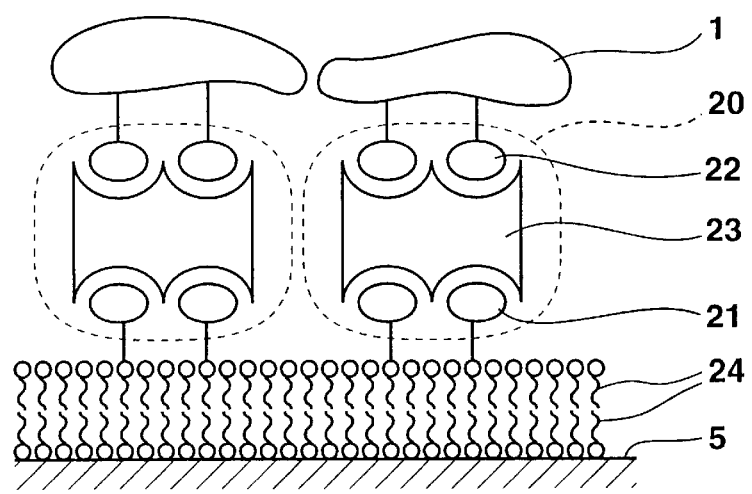
FIG. 2 shows an embodiment with a three-component molecular coupling system and a lipid double layer.

FIG. 2 shows an improved embodiment: A lipid double layer 24, which is much easier to produce, is applied to the solid carrier surface 5, its side facing away from the carrier surface 5 being coupled to a three-component molecular coupling system 20 via its first component 21. A second component 22 of the molecular coupling system 20 is covalently coupled to the macromolecules 1 to be examined. The two other components of the molecular coupling system 20 are connected to each other through a third component 23 which shows high bonding affinity for the components 21, 22.

A three-component molecular coupling system 20 opens also an almost unlimited variability with respect to the immobilization of macromolecules 1, to be examined, on carrier surfaces 5 provided with lipid films. In particular, the first component 21 and the second component 22 may be chemically identical. In preferred embodiments, the first and second components 21, 22 consist each of biotin, whereas the third component 23 is formed of avidin and/or streptavidin molecules.

Many macromolecules may be obtained already in biotinylated form.

Another system comprises as first and second components 21, 22 one antigen in each case, whereas the third component 23 may be the corresponding antibody. But also any number of other molecule combinations which can be coupled and which may form the molecular coupling system 23 is feasible.

For coupling the hydrophilic macromolecules 1, to be examined, to crystals (ZnSe, Ge) which can be used in particular in ATR (attenuated total reflection) IR spectroscopy, at first aqueous phospholipid solutions are applied onto the crystal, wherein approx. 10% of the lipids are biotinylated. During the drying process a lipid film is formed on the crystal. Then, dissolved streptavidin is attached at one or two of its four highly affine binding points to the exposed biotin residues of the lipid film. Consequently, the hydrophilic macromolecule 1 to be examined, e.g. a protein, is added in dissolved form. Said protein has been biotinylated before and is recognized specifically by streptavidin through the biotin residues. The crystal surface remains unharmed during the coating process. The lipid film with the immobilized proteins (streptavidin and protein to be examined) can be easily removed by means of a cloth such that the crystal can be coated as many times as required. The protein streptavidin, gained from streptomyces avidinii may be replaced by avidin which is isolated from the egg white.

Figure 3:
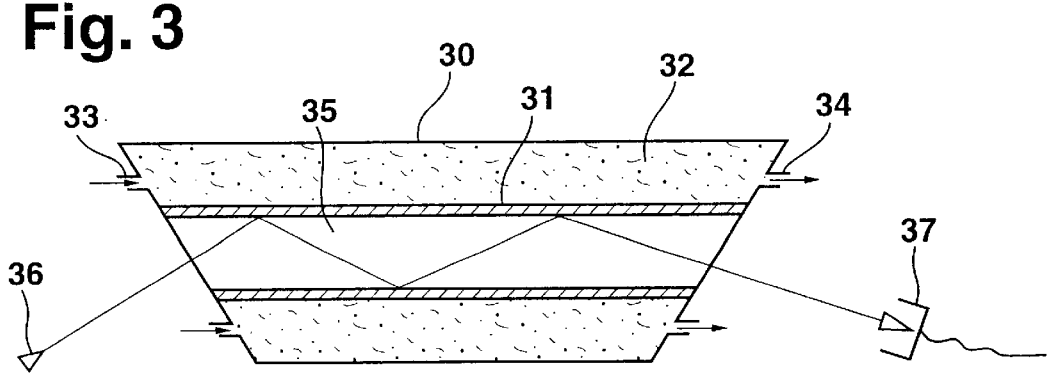
FIG. 3 shows a schematic longitudinal section through a flow cell for carrying out the examination method according to the invention.

FIG. 3 shows in a concrete manner a flow cell 30 for guiding the aqueous solution 32 past the solid carrier surface of an ATR crystal 35 with the immobilized hydrophilic macromolecules of the inventive arrangement 31 arranged thereon as described above. The aqueous solution 32 with the hydrophilic macromolecules to be examined is introduced via an inlet 33 into the flow cell 30 and drawn out via an outlet 34. For the optical measurement of molecular properties, in the example shown, MIR light 36 is irradiated into the ATR crystal 35 which records information on the macromolecules to be examined from the arrangement 31 according to the method of weakened total reflection infrared spectroscopy (ATR-IR) when passing through the ATR crystal. Afterwards, the MIR light 36 is detected in a suitable detection system 37.

Instead of MIR radiation e.g. also light from the near infrared area (NIR) can be used for investigation or also Raman dispersion may be carried out on the molecules to be investigated, wherein complementary molecular information for the information gained in the MIR range is basically obtained. Also feasible is the use of the inventive arrangement in other physical investigation methods, preferably by using electromagnetic radiation, however, not necessarily with optical methods (e.g. electron diffraction).

What is claimed is:

1. A device for investigating hydrophilic macromolecules in aqueous solutions, the device comprising:

a solid carrier onto which a lipid film has been applied;

a first antigen bound to said lipid film;

a second antigen bound to the hydrophilic macromolecules to be investigated;

an antibody bound to and connected between said first antigen and said second antigen, whereby the hydrophilic macromolecules are molecularly coupled to said lipid film and rendered immobile.

2. A device for investigating hydrophilic macromolecules in aqueous solutions, the device comprising:

an attenuated total reflection element;

a lipid film applied to an upper surface of said attenuated total reflection element;

a first component bound to said lipid film;

a second component, chemically identical to said first component, bound to the hydrophilic macromolecules;

a third component bound to and connected between said first component and said second component, whereby the hydrophilic macromolecules are molecularly coupled to said lipid film and rendered immobile;

means for irradiating at least one of near infrared and mid infrared radiation into said attenuated total reflection element;

means for detecting at least one of near infrared and mid infrared radiation subsequent to absorptive interaction with the hydrophilic macromolecules and transport through said attenuated total reflection element; and analysis means for attenuated total reflection spectroscopy, said analysis means communicating with said detecting means.

3. The device of claim 2, wherein said first and said second components are biotin and said third component is avidine and/or streptovidine.

4. The device of claim 3, wherein said lipid film is formed as a double layer.

5. The device of claim 3, wherein said lipid film is formed by packed vesicles.

6. The device of claim 2, wherein said first and second components are an antigen, and said third component is a corresponding antibody.

7. The device of claim 6, wherein said lipid film is formed by packed vesicles.

8. The device of claim 2, wherein said lipid film is formed as a double layer.

9. The device of claim 2, wherein said lipid film is formed by packed vesicles.

10. The device of claim 2, wherein the hydrophilic macromolecules to be examined are selected from the group consisting of proteins, peptides, DNA, RNA, whole procariotic and eucariotic cells.

11. The device of claim 2, wherein said attenuated total reflection element is an amorphous solid which is selected from the group consisting of silver halides, chalcogenides, glass and quartz.

12. The device of claim 2, wherein said attenuated total reflection element is a crystalline solid.

13. The device of claim 2, wherein said attenuated total reflection element comprises one of attenuated total reflection fibers, and attenuated total reflection crystals.

14. The device of claim 13, wherein said attenuated total reflection element is selected from a group consisting of zinc selenide, thallium bromide, germanium and diamond.

15. The device of claim 2, further comprising a flow cell for guiding the aqueous solution past a solid carrier surface of said attenuated total reflection element having immobilized hydrophilic macromolecules arranged thereon.

16. A device for investigating hydrophilic macromolecules, the device comprising:

an attenuated total reflection element;

a lipid film applied to an upper surface of said attenuated total reflection element;

a first component bound to said lipid film;

a second component, chemically identical to said first component, bound to the hydrophilic macromolecules;

a third component bound to and connected between said first component and said second component, whereby the hydrophilic macromolecules are molecularly coupled to said lipid film and rendered immobile;

a flow cell for passing an aqueous solution past immobilized hydrophilic macromolecules;

means for irradiating infrared radiation into said attenuated total reflection element for internal reflection of said infrared radiation through said attenuated total reflection element;

means for detecting said infrared radiation following passage of said infrared radiation through said attenuated total reflection element and subsequent to absorptive changes therein due to interaction with the hydrophilic macromolecules and said aqueous solution; and analysis means for attenuated total reflection spectroscopy, said analysis means communicating with said detecting means.

* * * * *